US009963495B2

(12) United States Patent
Liu et al.

(10) Patent No.: US 9,963,495 B2
(45) Date of Patent: May 8, 2018

(54) POLYPEPTIDES TARGETING VASCULAR ENDOTHELIAL GROWTH FACTOR RECEPTOR AND PROSTATE SPECIFIC MEMBRANE ANTIGEN

(71) Applicant: The Board of Trustees of the Leland Stanford Junior University, Stanford, CA (US)

(72) Inventors: Cassie J. Liu, Stanford, CA (US); Jennifer R. Cochran, Stanford, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 0 days. days.

(21) Appl. No.: 15/299,889

(22) Filed: Oct. 21, 2016

(65) Prior Publication Data

US 2017/0204150 A1 Jul. 20, 2017

Related U.S. Application Data

(60) Provisional application No. 62/247,028, filed on Oct. 27, 2015.

(51) Int. Cl.

| | |
|---|---|
| ***A61K 38/15*** | (2006.01) |
| ***C07K 14/515*** | (2006.01) |
| ***A61K 51/08*** | (2006.01) |
| *A61K 38/00* | (2006.01) |

(52) U.S. Cl.
CPC ............ *C07K 14/515* (2013.01); *A61K 51/08* (2013.01); *A61K 38/00* (2013.01); *C07K 2318/20* (2013.01); *C07K 2319/74* (2013.01)

(58) Field of Classification Search
None
See application file for complete search history.

(56) References Cited

U.S. PATENT DOCUMENTS

2012/0020889 A1* 1/2012 Cochran ............ A61K 38/1858 424/9.1

FOREIGN PATENT DOCUMENTS

WO 2002/081520 A2 10/2002

OTHER PUBLICATIONS

Boesen et al., "Single-chain vascular endothelial growth factor variant with antagonist activity", J Biol Chem., Oct. 25, 2002, pp. 40335-40341, 277 (43), American Society for Biochemistry and Molecular Biology, Inc., Rockville, MD.

* cited by examiner

*Primary Examiner* — Fred H Reynolds
(74) *Attorney, Agent, or Firm* — Pamela J. Sherwood; Bozicevic, Field & Francis LLP

(57) ABSTRACT

Polypeptides comprising a VEGF scaffold modified to bind to PSMA are provided, and bifunctional derivatives thereof that also bind to VEGFR. The polypeptides are useful in cancer imaging, cancer diagnosis, monitoring and treatment.

21 Claims, 7 Drawing Sheets
(5 of 7 Drawing Sheet(s) Filed in Color)

Fig. 2

<u>VEGFR2/PSMA sequence</u>

EVVKAMDVYQRSYCHPIETLVDIFQEYPDEIEYIFKPSCVPLMRCGGCC[NDAGL]ECVPTEESNITMQIMRIKPHQGQHIGEMSFLQHNKCECRPKKD

[LINKER]

EVVKFMDVYQRSYCHPIETLVDIFQEYP[SIASWNPWM]AFKPSCVPLMRCGGCCNDEGLECVPTEESNITMQIMR[NRLFRYLPV]RHIGEMSFLQHNKCECRPKKD

<u>Alternative VEGFR2/PSMA sequence</u>

EVVKAMDVYQRSYCHPIETLVDIFQEYPDEIEYIFKPSCVPLMRCGGCC[NDAGL]ECVPTEESNITMQIMRIKPHQGQHIGEMSFLQHNKCECRPKKD

[LINKER]

EVVKFMDVYQRSYCHPIETLVDIFQEYP[SIASWNPWM]AFKPSCVPLMRCGGCCNDEGLECVPTEESNITMQIMR[SYLKFWIRW]RHIGEMSFLQHNKCECRPKKD

Data is the half maximal Gdn-HCl concentration.

| | $c_{1/2}$ (M) |
|---|---|
| scVEGFmut | 4.5 ± 0.0 |
| VEGFR2/PSMA | 4.8 ± 0.2 |

Fig. 6

| Variant | VEGFR2-Fc $K_D$ (nM) | PSMA $K_D$ (nM) |
|---|---|---|
| scVEGFmut | 6.0 ± 0.5 | n/a |
| VEGFR2/PSMA | 4.6 ± 1 | 58 ± 20 |

| Variant | VEGFR2-Fc $K_D$ (nM) |
|---|---|
| scVEGFmut | 13 ± 5 |
| VEGFR2/PSMA | 13 ± 5 |

SEQUENCE LISTING

```
<160> NUMBER OF SEQ ID NOS: 12

<210> SEQ ID NO 1
<211> LENGTH: 121
<212> TYPE: PRT
<213> ORGANISM: Homo sapiens

<400> SEQUENCE: 1

Ala Pro Met Ala Glu Gly Gly Gly Gln Asn His His Glu Val Val Lys
1               5                   10                  15

Phe Met Asp Val Tyr Gln Arg Ser Tyr Cys His Pro Ile Glu Thr Leu
            20                  25                  30

Val Asp Ile Phe Gln Glu Tyr Pro Asp Glu Ile Glu Tyr Ile Phe Lys
        35                  40                  45

Pro Ser Cys Val Pro Leu Met Arg Cys Gly Gly Cys Cys Asn Asp Glu
    50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Lys Cys Asp Lys Pro Arg Arg
        115                 120


<210> SEQ ID NO 2
<211> LENGTH: 97
<212> TYPE: PRT
<213> ORGANISM: Homo sapiens

<400> SEQUENCE: 2

Glu Val Val Lys Phe Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
            20                  25                  30
```

```
Tyr Ile Phe Lys Pro Ser Cys Val Pro Leu Met Arg Cys Gly Gly Cys
        35                  40                  45

Cys Asn Asp Glu Gly Leu Glu Cys Val Pro Thr Glu Glu Ser Asn Ile
    50                  55                  60

Thr Met Gln Ile Met Arg Ile Lys Pro His Gln Gly Gln His Ile Gly
65                  70                  75                  80

Glu Met Ser Phe Leu Gln His Asn Lys Cys Glu Cys Arg Pro Lys Lys
                85                  90                  95

Asp


<210> SEQ ID NO 3
<211> LENGTH: 104
<212> TYPE: PRT
<213> ORGANISM: Homo sapiens

<400> SEQUENCE: 3

Glu Val Val Lys Phe Met Asp Val Tyr Gln Arg Ser Tyr Cys His Pro
1               5                   10                  15

Ile Glu Thr Leu Val Asp Ile Phe Gln Glu Tyr Pro Ser Ile Ala Ser
            20                  25                  30

Trp Asn Pro Trp Met Ala Phe Lys Pro Ser Cys Val Pro Leu Met Arg
        35                  40                  45

Cys Gly Gly Cys Cys Asn Asp Glu Gly Leu Glu Cys Val Pro Thr Glu
    50                  55                  60

Glu Ser Asn Ile Thr Met Gln Ile Met Arg Asn Arg Leu Phe Arg Tyr
65                  70                  75                  80

Leu Pro Val Arg His Ile Gly Glu Met Ser Phe Leu Gln His Asn Lys
                85                  90                  95

Cys Glu Cys Arg Pro Lys Lys Asp
            100


<210> SEQ ID NO 4
<211> LENGTH: 104
<212> TYPE: PRT
<213> ORGANISM: Homo sapiens

<400> SEQUENCE: 4

Glu Val Val Lys Phe Met Asp Val Tyr Gln Arg Ser Tyr Cys His Pro
1               5                   10                  15

Ile Glu Thr Leu Val Asp Ile Phe Gln Glu Tyr Pro Ser Ile Ala Ser
            20                  25                  30

Trp Asn Pro Trp Met Ala Phe Lys Pro Ser Cys Val Pro Leu Met Arg
        35                  40                  45

Cys Gly Gly Cys Cys Asn Asp Glu Gly Leu Glu Cys Val Pro Thr Glu
    50                  55                  60

Glu Ser Asn Ile Thr Met Gln Ile Met Arg Ser Tyr Leu Lys Phe Trp
65                  70                  75                  80

Ile Arg Trp Arg His Ile Gly Glu Met Ser Phe Leu Gln His Asn Lys
                85                  90                  95

Cys Glu Cys Arg Pro Lys Lys Asp
            100


<210> SEQ ID NO 5
<211> LENGTH: 97
<212> TYPE: PRT
<213> ORGANISM: Homo sapiens

<400> SEQUENCE: 5
```

```
Glu Val Val Lys Ala Met Asp Val Tyr Gln Arg Ser Tyr Cys His Pro
1               5                   10                  15

Ile Glu Thr Leu Val Asp Ile Phe Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Thr Glu Glu Ser Asn Ile
    50                  55                  60

Thr Met Gln Ile Met Arg Ile Lys Pro His Gln Gly Gln His Ile Gly
65                  70                  75                  80

Glu Met Ser Phe Leu Gln His Asn Lys Cys Glu Cys Arg Pro Lys Lys
                85                  90                  95

Asp


<210> SEQ ID NO 6
<211> LENGTH: 97
<212> TYPE: PRT
<213> ORGANISM: Homo sapiens

<400> SEQUENCE: 6

Glu Val Val Lys Ala Met Asp Val Tyr Gln Arg Ser Tyr Cys His Pro
1               5                   10                  15

Ile Glu Thr Leu Val Asp Ile Leu Gln Glu Tyr Pro Asp Glu Ile Glu
            20                  25                  30

Tyr Ile Phe Lys Pro Ser Cys Val Pro Leu Met Arg Cys Gly Gly Cys
        35                  40                  45

Cys Asn Asp Ala Gly Leu Glu Cys Val Pro Ala Glu Glu Ser Asn Ile
    50                  55                  60

Thr Met Gln Val Met Arg Ile Lys Pro His Gln Gly Gln His Ile Gly
65                  70                  75                  80

Glu Met Ser Phe Leu Gln His Asn Lys Cys Glu Cys Arg Pro Lys Lys
                85                  90                  95

Asp


<210> SEQ ID NO 7
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 7

Ser Ile Ala Ser Trp Asn Pro Trp Met
1               5


<210> SEQ ID NO 8
<211> LENGTH: 9
<212> TYPE: PRT
<213> ORGANISM: Artificial sequence
<220> FEATURE:
<223> OTHER INFORMATION: Synthetic polypeptide

<400> SEQUENCE: 8

Asn Arg Leu Phe Arg Tyr Leu Pro Val
1               5


<210> SEQ ID NO 9
<211> LENGTH: 9
<212> TYPE: PRT
```

-continued

<213> ORGANISM: Artificial sequence
<220> FEATURE:
<223> OTHER INFORMATION: Synthetic polypeptide

<400> SEQUENCE: 9

Ser Tyr Leu Lys Phe Trp Ile Arg Trp
1 5

<210> SEQ ID NO 10
<211> LENGTH: 19
<212> TYPE: PRT
<213> ORGANISM: Artificial sequence
<220> FEATURE:
<223> OTHER INFORMATION: Synthetic polypeptide

<400> SEQUENCE: 10

Gly Ser Thr Ser Gly Ser Gly Lys Ser Ser Glu Gly Lys Gly Gly Gly
1 5 10 15

Gly Gly Ser

<210> SEQ ID NO 11
<211> LENGTH: 14
<212> TYPE: PRT
<213> ORGANISM: Artificial sequence
<220> FEATURE:
<223> OTHER INFORMATION: Synthetic polypeptide

<400> SEQUENCE: 11

Gly Gly Gly Gly Ser Gly Gly Gly Gly Ser Gly Gly Gly Gly
1 5 10

<210> SEQ ID NO 12
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 12

Gly Gly Gly Gly Ser Gly Gly Gly Gly Ser Gly Gly Gly Gly Ser Gly
1 5 10 15

Gly Gly Gly Ser
20

POLYPEPTIDES TARGETING VASCULAR ENDOTHELIAL GROWTH FACTOR RECEPTOR AND PROSTATE SPECIFIC MEMBRANE ANTIGEN

CROSS REFERENCE

This application claims benefit of U.S. Provisional Patent Application No. 62/247,028, filed Oct. 27, 2015, which application is incorporated herein by reference in its entirety.

FEDERALLY SPONSORED RESEARCH AND DEVELOPMENT

This invention was made with Government support under contract W81XWH-12-1-0135 awarded by the Department of Defense. The Government has certain rights in the invention.

BACKGROUND OF THE INVENTION

A general concept of bispecific reagents is that they provide a physical connection of recombinant entities with at least two binding specificities. The ability to bind two different targets at a high affinity allows greater selectivity in treatment and imaging. For example, Papo et al. (2011) PNAS 108:14067-14072, mutagenized one pole of a single chain vascular endothelial growth factor (VEGF) ligand by introduction of an RGD loop, in order to provide a bispecific reagent that bound both VEGFR2 and $\alpha v\beta 3$ integrin. This provides a reagent that binds two different cell surface proteins to achieve a more complete blockage of angiogenesis-associated pathways.

VEGF plays a prominent role in tumor-associated vascular formation. VEGF-mediated signaling is mediated through its interactions with two receptor tyrosine kinases, VEGFR1 (Flt-1) and VEGFR2 (Flk-1 or KDR). VEGFR2, which is expressed in vascular endothelial cells, monocytes, macrophages, and hematopoietic stem cells, is the primary mediator of the mitogenic and angiogenic effects of VEGF. VEGF is a homodimeric ligand that binds two molecules of VEGFR2, one at each pole, thereby triggering receptor dimerization and activation, with a $K_D$ of around 100 pM. VEGF-A is the main ligand for VEGFR2, but proteolytically cleaved forms of VEGF-C and VEGF-D may also bind to and activate VEGFR2.

In addition to therapeutic uses, bispecific reagents can provide benefits for molecular imaging. The fundamental challenge for imaging is achieving a high signal over adjacent normal tissues, resulting in high image resolution. In therapy, the challenge is the delivery of tumoricidal doses of the therapeutic agent while sparing normal tissues from unacceptable toxicities. When using antibodies or fragments to target radioactivity to tumors, the binding specificity, pharmacokinetics and biodistribution have to be matched to the radionuclide, tumor, and disease setting for optimal results to be achieved. The nature and size of the immunoglobulin, or its smaller constructs, will determine how quickly it reaches the target antigen and clears from the blood, and the extent, penetration, and duration of its binding to the tumor vs. normal tissues.

Small molecules traditionally used for tumor imaging or therapy suffer from non-specificity. There is therefore a need for reagents that can leverage the advantages of bispecificity and high affinity for its targets, while maintaining an ideal size and stability for tumor targeting. Prostate cancer diagnosis suffers from inaccuracy due to a lack of a single, canonical prostate cancer biomarker. Bispecific antibodies and antibody fragments have been used to address this issue by targeting multiple involved biomarkers to increase specficity, but as tumor imaging tools these molecules are limited by issues of size and stability.

The present invention provides a solution for these issues.

PUBLICATIONS

Boesen et al. (2002) "Single-chain vascular endothelial growth factor variant with antagonist activity", *J Biol Chem* 277 (43), pp. 40335-40341, disclose the preparation of a single-chain VEGF variants.

WO02081520 by Thomas P. Boesen and Torben Halkier, filed Apr. 8, 2002, and entitled "Single Chain Dimeric Polypeptides", discloses a single-chain dimeric polypeptide which binds to an extracellular ligand-binding domain of VEGFR2 or VEGFR3 receptor and which functions as a receptor antagonist for prevention or treatment of a disease or condition involving increased signal transduction from or increased activation of the VEGFR2 and/or VEGFR3 receptor, e.g. to inhibit angiogenesis or lymphangiogenesis.

SUMMARY OF THE INVENTION

Compositions and methods of use relating to protein entities that bind to prostate specific membrane protein (PSMA), which proteins are based on a VEGF scaffold in which the VEGF loop 2 and loop 3 sequences are replaced with a PSMA binding motif to provide a PSMA binding chain. In some embodiments the VEGF scaffold is a VEGF-A 121 protein or truncated variant thereof, as provided in the sequences herein. In some embodiments the PSMA binding chain is joined through a disulfide or linker to a VEGF chain, to provide a bifunctional VEGF/PSMA binding protein.

Methods are provided that utilize the polypeptides of the invention for imaging normal tissue, abnormal tissue, precancerous tissue, cancer, and tumors. In other embodiments methods are provided for diagnosis of precancerous tissue, cancer, and tumors. In other embodiments the bifunctional VEGF/PSMA binding protein of the invention is used in the treatment of an individual having a vascularized tumor or cancer.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 2: provides amino acid sequences for exemplary scVEGF proteins modified to bifunctionally bind VEGFR and PSMA.

PSMA has a molecular weight of 24,735 Daltons, compared to antibodies having a molecular weight of ~150,000 Daltons. FIG. 4A. VEGFR2/PSMA retains the high stability of wild-type VEGF. FIG. 4B. It does not denature up to 95° C. and has a Gdn HCl melt midpoint of 4.8±0.2 M (vs scVEGFmut with a midpoint of 4.5±0.0 M).

FIG. 6: Binding affinity. For proteins displayed on the yeast cell surface, binding to VEGFR2 receptor is comparable to that of scVEGFmut. This indicates that mutating the loops does not greatly affect the non-mutated side. Binding to PSMA is mid-nanomolar affinity. In soluble form, scVEGFmut and VEGFR2/PSMA have nearly identical affinities to VEGFR2-Fc.

DETAILED DESCRIPTION OF THE EMBODIMENTS

Figure 1:
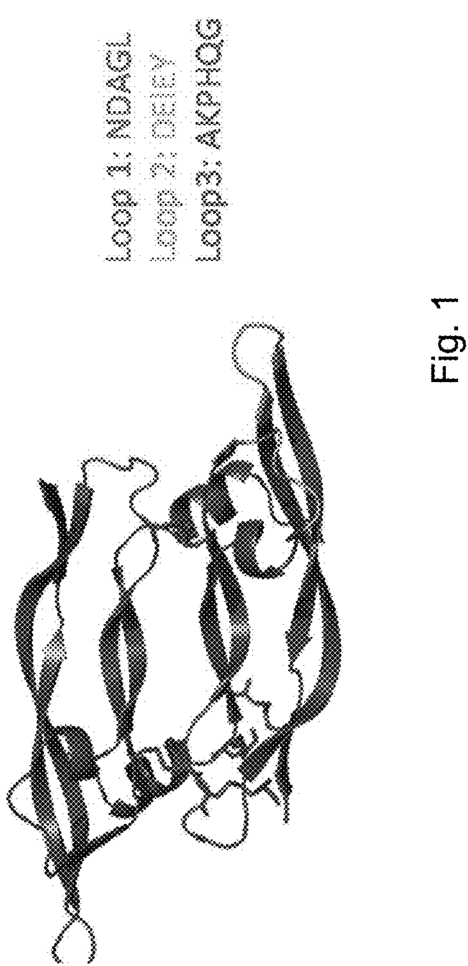
FIG. 1: shows the structure of scVEGFmut.
Figure 3:
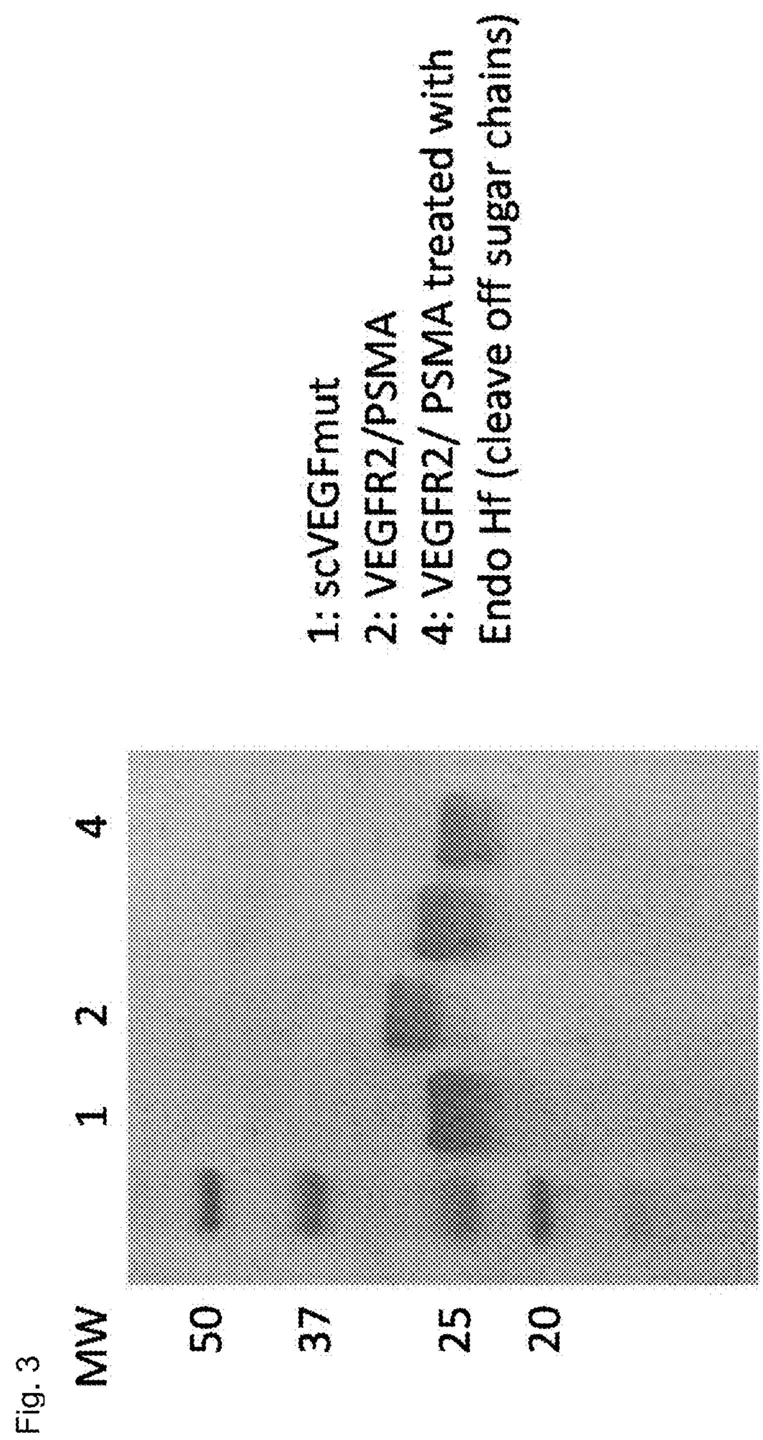
FIG. 3: VEGFR2/PSMA protein can be made in *Pichia pastoris* yeast secretion system.
Figure 4A:
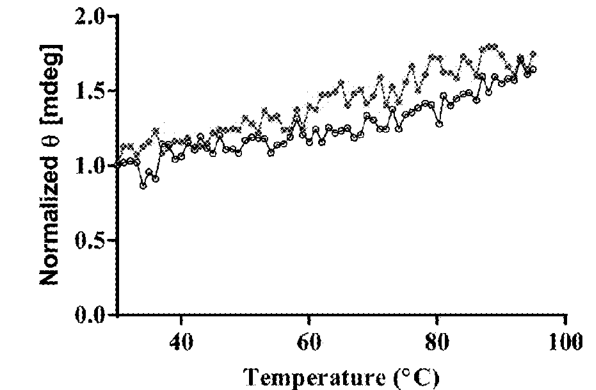
FIG. 4A-4B: Advantages of VEGFR2/PSMA are size and stability. For tumor imaging, smaller size generally indicates faster clearance and better tumor penetration. VEGFR2/
Figure 4B:
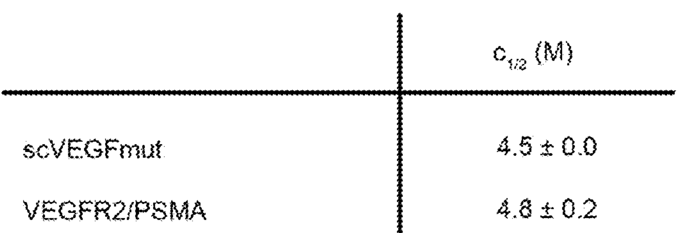
Figure 5:
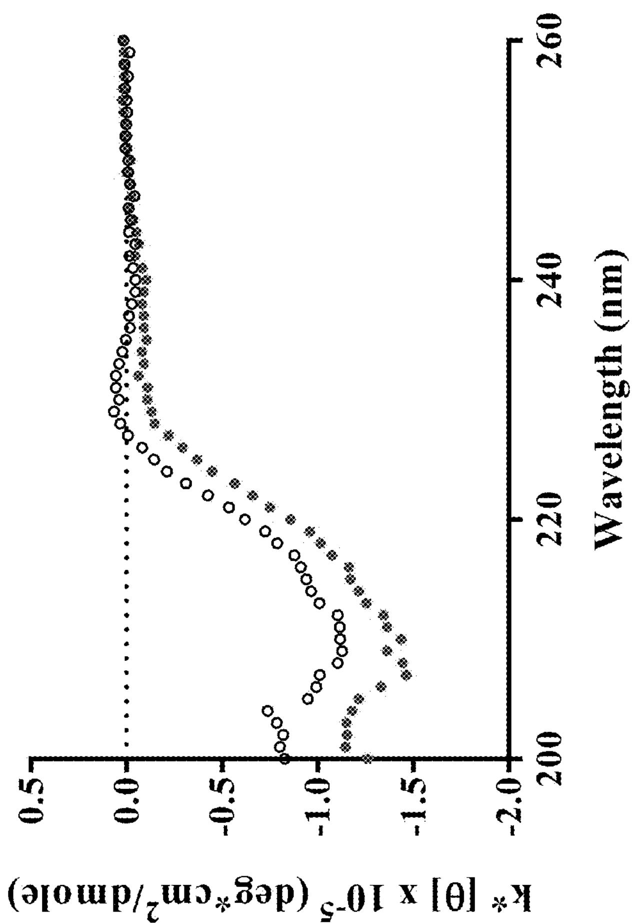
FIG. 5: Circular dichroism (CD) can analyze a protein's secondary structure in bulk. scVEGFmut has a spectra consistent with a mostly β-sheet structure. VEGFR2/PSMA has a nearly identical spectra, indicating that mutating the loops does not change the overall structure.
Figure 7A:
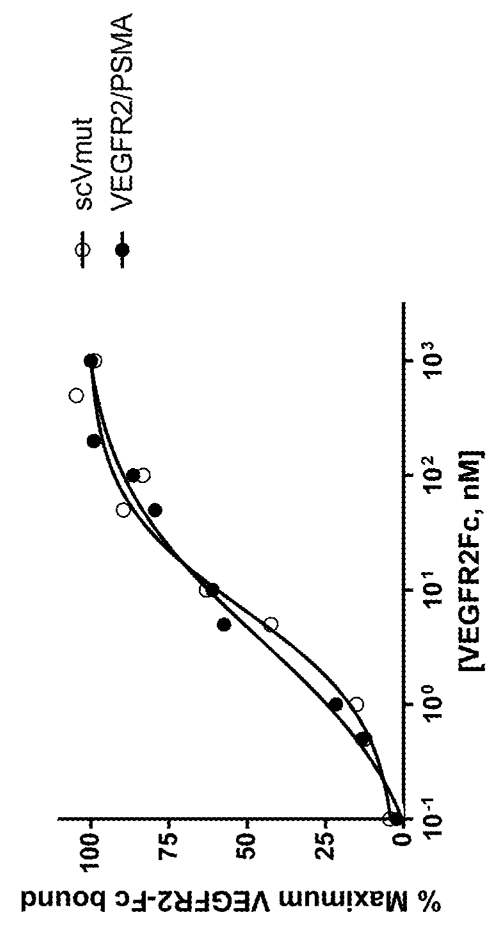
FIG. 7A-7B show binding curves for protein displayed in the yeast cell surface of the scaffold protein and the VEGFR/PSMA binding protein to (FIG. 7A) VEGFR2 and to (FIG. 7B) PSMA.
Figure 7B:
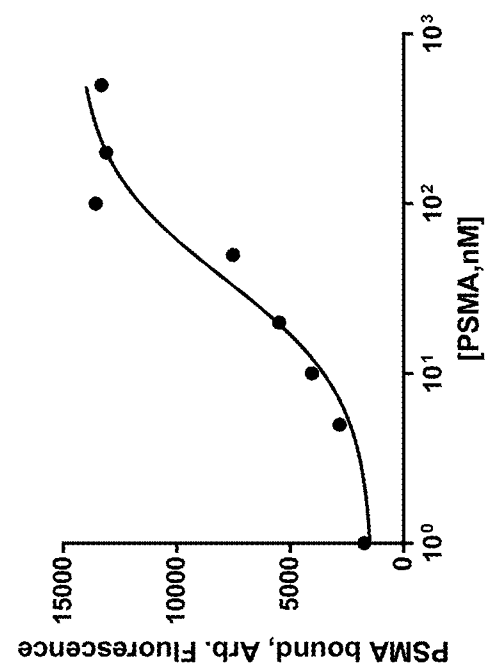

Several embodiments are described below with reference to examples and applications for illustration. It should be understood that numerous specific details, relationships, and methods are set forth to provide a full understanding of the features described herein. A skilled artisan in the relevant art, however, will readily recognize that the features described herein, in some embodiments, are practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

The term "about" or "approximately" can mean within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

VEGF, or Vascular Endothelial Growth Factor, refers to a family of signaling proteins that stimulate angiogenesis, vasculogenesis and lymphangiogenesis. Members of the VEGF family include VEGF-A, VEGF-B, VEGF-C, VEGF-D, and P1GF (Placental Growth Factor). If the particular member of VEGF is not specified, then VEGF means any of VEGF-A, VEGF-B, VEGF-C, VEGF-D, and P1GF. Within this application, amino acid residue numbering of any VEGF monomer commences at residue 13 with respect to the mature human wild type VEGF-A sequence. When referred to herein, Loop 1 of VEGF-A means amino acid residues 62 to 67 (with respect to the mature human wild type VEGF-A sequence); Loop 2 means amino acid residues 39 to 46 (with respect to the mature human wild type VEGF-A sequence); and Loop 3 means amino acid residues 83-89 (with respect to the mature human wild type VEGF-A sequence). Loops 1, 2, and 3 of other VEGF family members can be similarly defined or inferred by homology.

"VEGF" is a secreted disulfide-linked homodimer that selectively stimulates endothelial cells to proliferate, migrate, and produce matrix-degrading enzymes, all of which are processes required for the formation of new vessels. In addition to being the only known endothelial cell specific mitogen, VEGF is unique among angiogenic growth factors in its ability to induce a transient increase in blood vessel permeability to macromolecules.

The human VEGF gene is organized in eight exons, separated by seven introns. Alternative exon splicing of the VEGF gene results in the generation of at least five different molecular species, having respectively 121, 145, 165, 189 and 206 amino acids (VEGF-121, VEGF-145, VEGF-165, VEGF-189, VEGF-206); these isoforms differ not only in their molecular weight but also in their biological properties, such as the ability to bind to cell surface heparin sulfate proteoglycans. VEGF-165 is the predominant molecular species produced by a variety of normal and transformed cells (Houck et al. (1991), Mol Endocrinol 5, pp. 1806-1814; Carmeliet et al. (1999), Nature Med 5, pp. 495-502).

VEGF signaling is mediated largely via two homologous, endothelium-specific tyrosine kinase receptors, VEGFR1 (Flt-1 aka fms-like tyrosine kinase 1) and VEGFR2 (Flk-1/KDR aka kinase domain receptor) whose expression is highly restricted to cells of endothelial origin (de Vries et al. (1992), Science 255, pp. 989-991; Millauer et al. (1993), Cell 72, pp. 835-846; Terman et al. (1991), Oncogene 6, pp. 519-524). Both receptors have an extracellular domain consisting of seven IgG-like domains, a transmembrane domain and an intracellular tyrosine kinase domain. The affinity of VEGFR1 for VEGF (Kd=1-20 pM) is higher compared to that of VEGFR2 (Kd=50-770 pM) (Brown et al. (1997) in "Control of Angiogenesis" (Goldberg and Rosen, eds.), Birkhauser, Basel, pp. 233-269; de Vries et al. (1992), Science 255, pp. 989-991; Terman et al. (1992,) Biochem Biophys Res Commun 187, pp. 1579-1586).

While VEGFR1 is essential for physiologic and developmental angiogenesis, VEGFR2 is the major mediator of the mitogenic, angiogenic and permeability-enhancing effects of VEGF and, thus, a major factor in tumor angiogenesis; as a consequence, VEGFR2 overexpression can be observed on tumor endothelial cells of angiogenic vessels in many cancers (Tucker G C (2006), Curr Oncol Rep 8, pp. 96-103; Parker et al. (2005), Protein Eng Des Sel 18, pp. 435-44; Boesen et al. (2002), J Biol Chem 277, pp. 40335-41; Siemeister et al. (1998), Proc Natl Acad Sci USA 95, pp. 4625-9; Cai et al. (2005), Biotechniques 39, pp. S6-S17; Haubner R (2006), Eur J Nucl Med Mol Imaging 33 Suppl 1, pp. 54-63).

The term "scVEGF" as used herein describes a single-chain variant of VEGF, particularly a single chain in which two "poles" of VEGF are joined by a linker. An scVEGF may be an antagonistic variant. For example Boesen, et al., supra provide a single-chain variant of VEGF121 (a common isoform of VEGF-A that does not require heparin binding) is prepared by linking the C-terminus of chain 1 to the N-terminus of chain 2 by a 14-amino acid flexible linker. In addition, mutations were added to both chains at one pole of the ligand in order to prevent binding of VEGFR2 at one receptor-binding site. The result is a protein that can bind only a single molecule of VEGFR2, and is antagonistic because it prevents receptor dimerization and activation.

The VEGF dimer contains two receptor binding interfaces lying on each pole of the molecule. Each of the two binding interfaces is typically able to contact one receptor monomer (either VEGFR1 or VEGFR2), thereby inducing receptor dimerization and activation. Consequently, an asymmetric VEGF variant that contains only one receptor binding interface at one pole of the dimer is not able to induce receptor dimerization and activation and, therefore, act as a VEGF antagonist (Siemeister et al. (1998), Proc Natl Acad Sci USA 95, pp. 4625-4629).

"scVEGF variant" describes a single-chain version of a VEGF variant polypeptide, i.e. a single chain molecule in which two VEGF monomer subunits are joined for example by a peptide linker, and where the sequence of the VEGF chains differs from the native sequence, for example by introduction of amino acid substitutions that provide a PSMA binding motif. As used herein, the terms "single chain VEGF variant", and "scVEGF variant" are used interchangeably.

As used herein, "pole" or "face" refers to a VEGFR binding interface of a VEGF variant polypeptide. The "pole" or "face" comprises amino acids residues from the first VEGF monomer subunit and the second VEGF monomer subunit. Each pole binds to one VEGFR molecule. "Pole" and "face" are used interchangeably.

"Mutant" refers to a polypeptide that differs in some way from a reference wild-type polypeptide. The polypeptide retains biological properties of the reference wild-type (e.g., naturally occurring) polypeptide. In some embodiments, the polypeptide has biological properties that differ from the reference wild-type polypeptide. In some embodiments, the mutant has a mutation in which the polypeptide chain has a replacement, addition, insertion, omission, substitution or deletion, or a combination thereof of the amino acid residues.

An "anti-VEGF agent" means an inhibitor of VEGF signaling, for example a competitive antagonist, a non-competitive antagonist, an uncompetitive antagonist, a silent antagonist, a partial agonist, or an inverse agonist.

Prostate-specific membrane antigen (PSMA), also referred to as folate hydrolase I is a type II membrane protein originally characterized by the murine monoclonal antibody (mAb) 7E11-05.3 and is expressed in all forms of prostate tissue, including carcinoma. The PSMA protein has a unique 3-part structure: a 19-amino-acid internal portion, a 24-amino-acid transmembrane portion, and a 707-amino-acid external portion. The genetic sequence may be accessed at Genbank, NM_004476. The PSMA gene is located on the short arm of chromosome 11 in a region that is not commonly deleted in prostate cancer. PSMA acts as a glutamate-preferring carboxypeptidase. The use of PSMA as a therapeutic antigenic target has been tested with delivery of radionuclides, and in immunotherapy.

PSMA has both glutamate carboxypeptidase II activity that cleaves α-linked glutamate from N-acetylaspartyl glutamate (NAALADase activity) and γ-linked glutamates from polyglutamated folates sequentially (folate hydrolase activity). Although its mechanism in not yet known, PSMA (a folate hydrolase) may facilitate prostate carcinogenesis by enhancing the proliferative and invasive capability of prostate cancer cells (which can be blocked by folic acid).

Both expression and enzymatic activity of PSMA are elevated in prostate cancer and in the neovasculature of many solid tumors, with expression levels closely correlated with disease grade (Lapidus R G, Prostate, 2000). Interestingly, endothelial cells of the neovasculature of almost all solid tumors express PSMA but not cells in the neovasculature associated with normal tissues (Silver D A, Clin Cancer Res 1997). In particular, there is an increase in both expression and enzymatic activity of PSMA in aggressive prostate tumors. The highest levels of PSMA expression are associated with high-grade, hormone-refractory and metastatic prostate cancer (Kawakami M, Cancer Res., 1997). In fact, PSMA mRNA is upregulated upon androgen withdrawal (Israeli R S, Cancer Res., 1994). In general, PSMA expression is ubiquitous, with expression in nearly all tumor sites. These properties have made PSMA an ideal target for developmental prostate cancer imaging agents and therapeutics, especially in advanced disease.

PSMA has been used in the ProstaScint® scan (Cytogen Corporation, Princeton, N.J.), which links mAb 7E11 to $^{111}$indium to produce a radiodiagnostic marker, $^{111}$indium-capromab pendetide. The majority of studies in high-risk metastatic prostate cancer and recurrent prostate cancer have demonstrated a sensitivity rate of 60% to 80% and a specificity rate of 70% to 90%, which are better than the accuracy of current CT scans or MRIs. The combination of algorithms and ProstaScint scan provided an improved 72% positive predictive value for metastatic disease. As a result of limitations inherent to SPECT imaging, ProstaScint imaging techniques continue to evolve in an attempt to improve accuracy and clinical utility. In addition, PSMA is being used as a radiographic imaging target by newer, second-generation antibodies that bind the external portion of PSMA. PSMA expression may also be a predictor of disease recurrence in prostate cancer patients. In a multivariate analysis, PSMA expression independently predicted the likelihood of biochemical recurrence.

"Amino acid" refers to naturally occurring amino acids, non-naturally occurring amino acids, and amino acid analogs, and to the D or L stereoisomers of each.

The terms "peptide", "polypeptide", and "amino acid sequence" refer to a chain of amino acids. "Peptide", "polypeptide", and "amino acid sequence" are used interchangeably.

The terms "peptide linker", "polypeptide linker" or "amino acid" refer to a chain of amino acids that link one VEGF monomer subunit to another VEGF monomer subunit. The terms are used interchangeably.

The term "domain" as used herein describes a discrete portion of a protein assumed to fold independently of the rest of the protein and possessing its own function. The term "single domain" as used herein describes the presence of one domain in a protein.

The terms "polypeptide" and "polypeptides" as used herein include proteins and fragments thereof. Polypeptides are disclosed herein as amino acid residue sequences. Those sequences are written left to right in the direction from the amino to the carboxy terminus or N to C terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Identity," as known in the art, is a relationship between two or more polypeptide or protein sequences, as determined by comparing the sequences. In the art, "identity" also refers to the degree of sequence relatedness between polypeptides or proteins, as determined by the match between strings of such sequences. "Identity" can be readily calculated by known bioinformational methods.

The term "variant" refers to a polypeptide or protein that differs from a reference polypeptide or protein, but retains essential properties. A typical variant of a polypeptide differs in amino acid sequence from another, reference polypeptide. Generally, differences are limited so that the sequences of the reference polypeptide and the variant are closely similar overall (homologous) and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. The term "identical or essentially similar single-chain VEGF variants" as used herein include variants having more than 50% sequence identity to the single-chain VEGF variants disclosed in embodiments of the present invention.

A conservative variant may be a protein or peptide motif that is substantially similar to the reference sequence, e.g. differing by up to one, up to two, up to 3 amino acid residues. A conservative substitution may be a conservative substitution as known in the art (for example see Yamplolsky et al. (2005) Genetics 170(4): 1459-1472, herein specifically incorporated by reference.

Conservative amino acid substitutions are likely to have minimal impact on the activity of the resultant protein. Further information about conservative substitutions can be found, for instance, in Ben Bassat et al. (J. Bacteriol, 169:751-757, 1987), O'Regan et al. (Gene, 77:237-251, 1989), Sahin-Toth et al. (Protein ScL, 3:240-247, 1994), Hochuli et al (Bio/Technology, 6:1321-1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., Proc. Natl. Acad. Sci. USA, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. For example, conservative substitutions may be those set forth in the table below:

| Original Residue | Very Highly-Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

The terms "mutant" and "clone" are employed broadly to refer to a protein that differs in some way from a reference wild-type protein, where the protein may retain biological properties of the reference wild-type (e.g., naturally occurring) protein, or may have biological properties that differ from the reference wild-type protein. For the purposes of the invention reference may be made to a "modified VEGF receptor binding site", which differs in amino acid sequence from the native polypeptide but which retains properties of interest. The term "biological property" of the subject proteins includes, but is not limited to, biological interactions in cancer and/or ischemic or hypoxic related diseases, in vivo and/or in vitro stability (e.g., half-life), and the like. Mutants and clones can include single amino acid changes (point mutations), deletions of one or more amino acids (point-deletions), N-terminal truncations, C-terminal truncations, insertions, and the like. Mutants and clones can be generated using standard techniques of molecular biology.

"Purified" or "substantially purified" denotes that the indicated molecule is present in the substantial absence of other biological macromolecules, for example, polynucleotides, proteins, and the like. In some embodiments, the molecule is purified such that it constitutes at least 95% by weight, for example, at least 99% by weight, of the indicated biological macromolecules present. In some embodiments, water, buffers, and other small molecules with a molecular weight of less than 1000 Daltons, are present in any amount.

"Isolated" as used herein refers to a molecule separated from at least one other component present with the molecule in its natural source. In some embodiments, the molecule is isolated such that it constitutes greater than 50% by weight, for example, at least 75% by weight, of the indicated biological macromolecules present.

The terms "individual," "patient," or "subject" are used interchangeably. As used herein, they mean any mammal (i.e. species of any orders, families, and genus within the taxonomic classification animalia: chordata: vertebrata: mammalia). In some embodiments, the mammal is a human. None of the terms require or are limited to situation characterized by the supervision (e.g. constant or intermittent) of a health care worker (e.g. a doctor, a registered nurse, a nurse practitioner, a physician's assistant, an orderly, or a hospice worker).

"Treating" or "treatment" of a state, disorder or condition (e.g., cancer) includes: (1) preventing or delaying the appearance of clinical or sub-clinical symptoms of the state, disorder or condition developing in a mammal that is afflicted with or predisposed to the state, disorder or condition but does not yet experience or display clinical or subclinical symptoms of the state, disorder or condition; and/or (2) inhibiting the state, disorder or condition, including arresting, reducing or delaying the development of the disease or a relapse thereof (in case of maintenance treatment) or at least one clinical or sub-clinical symptom thereof; and/or (3) relieving the disease, e.g., causing regression of the state, disorder or condition or at least one of its clinical or sub-clinical symptoms including without limitation a decrease in tumor size or numbers of cancer cells present in the subject; and/or (4) causing a decrease in the severity of one or more symptoms of the disease. The benefit to a subject to be treated is either statistically significant or at least perceptible to the patient or to the physician.

"Angiogenic disorder" as used herein, means any condition or disorder that is associated with or that results from pathological angiogenesis, or that is facilitated by neovascularization (e.g., a tumor that is dependent upon neovascularization).

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are herein described.

Modifications and changes can be made in the structure of the polypeptides and proteins of this disclosure and still result in a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's or protein's biological functional activity, certain amino acid sequence substitutions can be made in a polypeptide or protein sequence and nevertheless obtain a polypeptide or protein with like properties.

Polypeptide Compositions

Provided herein are compositions and methods related to proteins based on a VEGF scaffold that specifically bind to the cancer target PSMA. Optionally the protein also binds to VEGFR. Such proteins include without limitation any of the VEGF polypeptides set forth herein, which comprise the modification of replacing amino acid residues of loop 2 or loop 3 in one VEGF pole with a candidate motif or library that binds to PSMA. The PSMA binding motif may be a peptide sequence known in the art or may be designed through directed evolution, where a random or semi-random assortment of sequences is inserted into a permissive loop and screened for binding. In some embodiments the VEGF loop 3 sequence IKPHQG (for wild-type) or AKPHQG for the VEGFmut variant, is replaced with a PSMA binding motif. In some embodiments the VEGF loop 2 sequence, DEWY, is replaced with a PSMA binding motif. In some embodiments a modification of the loop 1 sequence is additionally made.

In some embodiments, the PSMA binding loop replaces loop 2, or loop 3 of the first or the second VEGF monomer subunit, or any combinations thereof. In some embodiments, a PSMA binding moiety comprises a mutated chain of VEGF, in which the native sequence at loop 2 and loop 3 is replaced with PSMA binding motifs. In some embodiments the loop 2 sequence is replaced with the PSMA binding motif SIASWNPWM or a conservative variant thereof. In some embodiments the loop 3 sequence is replaced with a PSMA binding motif selected from NRLFRYLPV or SYLKFWIRW, or a conservative variant thereof. Generally a PSMA binding moiety of interest comprises both a loop 2 and a loop 3 substitution with PSMA binding motifs. The amino acid substitution Q89R or Q89K may be combined with the presence of the PSMA binding motifs.

The polypeptide binds to PSMA specifically, e.g. with a Kd less than about 500 nM, less than about 250 nM, less than about 100 nM, less than about 50 nM, less than about 25 nM, less than about 10 nM, less than about 1 nM. Screening for PSMA binding may be performed, for example, in an affinity selection coupled with mutagenesis of the binding motifs or the VEGF scaffold protein in order to select for a high affinity variant.

An exemplary VEGF scaffold may be engineered from the monomer VEGF-121 (SEQ ID NO:1), but contain only the 97-amino acid core region of VEGF-121 (SEQ ID NO:2), and have truncated N- and C-termini relative to VEGF-121. In some embodiments, the VEGF scaffold further comprises one or more of the amino acid modifications: I46A; Q89R, Q89K, F36L, T71A, I80V (where numbering of amino acids is made relative to the numbering of SEQ ID NO:1). Exemplary VEGFR/PSMA binding sequences are provided in FIG. 2. Sequences include, without limitation, a polypeptide chain set forth in SEQ ID NO:3 or SEQ ID NO:5, which comprise PSMA binding motifs. Such a polypeptide chain is optionally linked to a VEGF chain, e.g. as set forth in SEQ ID NO:1, SEQ ID NO:2, SEQ ID NO:5 or SEQ ID NO:6, joined through a peptide linker or disulfide bridge.

In some embodiments of the invention, the polypeptide chain modified to bind to PSMA is joined through a peptide linker or disulfide bridge to a VEGF chain, which may be referred to herein as a VEGF/PSMA bifunctional protein. Such a bifunctional protein may be described by the formula:

A-L-B, wherein

A is a first VEGF monomer subunit;

B is a second VEGF monomer subunit modified to comprise one or more PSMA binding motifs; and L is a peptide linker having 1 to 20 amino acids.

In some embodiments, L is a peptide linker having a formula selected from: $(GS)_n$, wherein n is an integer from 6 to 15; $(G_2S)_n$, wherein n is an integer from 4 to 10; $(G_3S)_n$, wherein n is an integer from 3 to 8; $(G_4S)_n$, wherein n is an integer from 2 to 6; $(G)_n$, wherein n is an integer from 12 to 30; and $(S)_n$, wherein n is an integer from 12 to 30. In some embodiments, L is selected from the group consisting of: GSTSGSGKSSEGKGGGGGS; GGGGSGGGGSGGGG; and GGGGSGGGGSGGGGSGGGGS.

The bifunctional protein may bind specifically to a VEGF receptor and PSMA without activating the VEGF receptor, thereby acting as an antagonist of VEGF. In some embodiments, the VEGFR is VEGFR1. In some embodiments, the VEGFR is VEGFR2. In some embodiments, at least one of the VEGF monomer subunits is a VEGF-A monomer. In some embodiments, the VEGF-A monomer is $VEGF_{165}$. In some embodiments, the VEGF-A monomer is $VEGF_{165b}$. In some embodiments, the VEGF-A monomer is $VEGF_{121}$. In some embodiments, the VEGF-A monomer is $VEGF_{145}$. In some embodiments, the VEGF-A monomer is $VEGF_{189}$. In some embodiments, the VEGF-A monomer is $VEGF_{206}$. In some embodiments, at least one of the VEGF monomer subunits is a VEGF-B subunit. In some embodiments, at least one of the VEGF monomer subunits is a VEGF-C subunit. In some embodiments, at least one of the VEGF monomer subunits is a VEGF-D subunit. In some embodiments, at least one of the VEGF monomer subunits is a P1GF. In some embodiments, the first VEGF monomer subunit and the second VEGF monomer subunit are each independently a VEGF-A monomer.

In some embodiments, the first VEGF monomer subunit of the VEGF variant polypeptide comprises one or more mutations. In some embodiments, the second VEGF monomer subunit of the VEGF variant polypeptide comprises one or more mutations in addition to the PSMA binding motifs. In some embodiments, the first and second VEGF monomer subunits of the VEGF variant polypeptide each independently comprise one or more mutations. In some embodiments, the first VEGF monomer subunit comprises a mutation selected from the group consisting of: V14A, V14I, V15A, K16R, F17L, M18R, D19G, Q22R, R23K, I29V, L32S, I35V, F36L, F36S, D41N, E42K, E44G, Y45H, F47S, K48E, P49L, S50P, P53S, G58S, C60Y, D63H, D63N, D63G, I76T, M78V, M81T, M81V, R82G, H86Y, Q87R, Q89H, H90R, I91T, I91V, N100D, and K101E. In some embodiments, the first VEGF monomer subunit comprises a mutation selected from the group consisting of F36L, E44G, D63G, and Q87R. In some embodiments, the first VEGF monomer subunit comprises a mutation selected from the group consisting of F36L, E44G, and Q87R. Mutations of interest include, without limitation, those set for in U.S. Pat. No. 8,741,839; U.S. provisional application 62/104,590; and U.S. provisional application 62/104,612; each herein specifically incorporated by reference, in particular with respect to the identification of amino acid substitutions in VEGF.

In some embodiments, the VEGF variant polypeptide comprises at least one amino acid substitution in at least one VEGF monomer subunit. In some embodiments, the VEGF variant polypeptide comprises at least two amino acid substitutions, at least 3 amino acid substitutions, at least 4 amino acid substitutions or at least 5 amino acid substitutions in at least one or both of the VEGF monomer subunits. In addition to naturally occurring amino acids, non-naturally occurring amino acids, or modified amino acids, are also contemplated and within the scope.

In some embodiments, the VEGF variant polypeptide comprises a portion of a full length active monomer, e.g., peptides that are not full length proteins. In some embodiments, the portion of a full length active monomer is obtained by substitution, replacement, addition, insertion, omission and/or deletion of an amino acid of these amino acid sequences. In some embodiments, the portion of a full length active monomer is linked with other peptides or polypeptides or with further chemical groups such as glycosyl groups, lipids, phosphates, acetyl groups or the like.

In certain embodiments, the VEGF/PSMA bifunctional protein comprises an immunoglobulin Fc region fused to the VEGF/PSMA bifunctional protein. In some embodiments, the VEGF/PSMA bifunctional polypeptide further comprises a toxin. In some embodiments, the toxin is selected from the group consisting of a *Pseudomonas* exotoxin (PE), a *Diphtheria* toxin (DT), ricin toxin, abrin toxin, anthrax toxins, shiga toxin, botulism toxin, tetanus toxin, cholera toxin, maitotoxin, palytoxin, ciguatoxin, textilotoxin, batrachotoxin, alpha conotoxin, taipoxin, tetrodotoxin, alpha tityustoxin, saxitoxin, anatoxin, microcystin, aconitine, exfoliatin toxins A, exfoliatin B, an enterotoxin, toxic shock syndrome toxin (TSST-I), *Y. pestis* toxin and a gas gangrene toxin. In some embodiments, the toxin is attached to the N-terminus of the VEGF variant. In some embodiments, the toxin is attached to the C-terminus of the VEGF variant. In some embodiments, the toxin is attached to the first or the second VEGF monomer subunit.

In some embodiments, a peptide linker is used to form a VEGF/PSMA bifunctional protein in a single chain conformation. In some embodiments, a peptide linker does not hinder the ability of the single chain molecule to bind a VEGF receptor. In some embodiments, a peptide linker does not hinder the ability of the single chain molecule to bind PSMA.

In some embodiments, the peptide linker ranges from about 2 to about 50 or more amino acids in length. For instance, in some embodiments, the peptide linker comprises about 2, 3, 4, 5, 6, 7, 8, 9, 10, 10-15, or 15-20 amino acids. In some embodiments, the peptide linker is 14-20 amino acids. In some embodiments, the peptide linker is 14 amino acids. In some embodiments, the peptide linker is 15 amino acids. In some embodiments, the peptide linker is 16 amino acids. In some embodiments, the peptide linker is 17 amino acids. In some embodiments, the peptide linker is 18 amino acids. In some embodiments, the peptide linker is 19 amino acids. In some embodiments, the peptide linker is 20 amino acids. In some embodiments, the peptide linker is Gly-Ser or contains Gly-Ser. In some embodiments, the peptide linker is a glycine-rich polypeptide chain.

Disclosed herein, in certain embodiments, are methods of treating an angiogenic disorder in an individual in need thereof, comprising administering to the individual a the VEGF/PSMA bifunctional protein disclosed herein. In some embodiments, the angiogenic disorder is a cancer. In some embodiments, the cancer is prostate cancer. In other embodiments the cancer is breast cancer, lung cancer, esophageal cancer, colon cancer, rectal cancer, liver cancer, urinary tract cancer (e.g., bladder cancer), kidney cancer, lung cancer (e.g., non-small cell lung cancer), ovarian cancer, cervical cancer, endometrial cancer, pancreatic cancer, stomach cancer, thyroid cancer, skin cancer (e.g., melanoma), hematopoietic cancers of lymphoid or myeloid lineage, head and neck cancer, nasopharyngeal carcinoma (NPC), glioblastoma, teratocarcinoma, neuroblastoma, adenocarcinoma, cancers of mesenchymal origin such as a fibrosarcoma or rhabdomyosarcoma, soft tissue sarcoma and carcinoma, choriocarcinioma, hepatoblastoma, Karposi's sarcoma or Wilm's tumor.

In some such embodiments, one pole of the VEGF/PSMA bifunctional protein comprises an intact VEGFR binding site such that this pole is able to bind to VEGFR. In some embodiments, at least one pole of the VEGF/PSMA bifunctional protein is not able to bind to a VEGFR, but binds specifically to PSMA. In some embodiments, upon binding of the VEGF/PSMA bifunctional protein to a VEGFR, the VEGFR is not activated. This thereby antagonizes VEGF-stimulated receptor autophosphorylation and propagation of downstream signaling resulting in inhibition of angiogenesis.

Without being bound to any one theory, the VEGF/PSMA bifunctional proteins disclosed herein are able to antagonize a VEGFR and subsequent signaling induced by VEGFR activation, because one pole of the VEGF variant polypeptide has an intact VEGFR binding site. This pole of the VEGF variant polypeptide is able to bind to a VEGFR, while the other pole of the VEGF variant polypeptide contains the PSMA binding motifs and thus does not bind to VEGFR, which prevents VEGFR dimerization and activation. The binding to PSMA can target the protein to PSMA expressing cells, which include without limitation prostate cancer cells.

Polypeptides can be produced through recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar in vivo activity.

The VEGF/PSMA bifunctional protein or single chains thereof can be produced through recombinant methods or chemical synthesis methods known to the skilled artisan. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent," as used herein, refers to a protein capable of exhibiting a substantially similar in vivo activity.

The VEGF/PSMA bifunctional protein or single chains thereof may be produced by recombinant DNA technology using techniques well known in the art. Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

As an option to recombinant methods, VEGF/PSMA bifunctional protein or single chains thereof can be chemically synthesized. Such methods typically include solid-state approaches, but can also utilize solution-based chemistries and combinations or combinations of solid-state and solution approaches. Examples of solid-state methodologies for synthesizing proteins are described by Merrifield (1963) J. Am. Chem. Soc. 85:2149; and Houghten (1985) Proc. Natl. Acad. Sci., 82:5131. Fragments of polypeptides of the invention proteins can be synthesized and then joined together. Methods for conducting such reactions are described by Grant (1992) Synthetic Peptides: A User Guide, W.H. Freeman and Co., N.Y.; and in "Principles of Peptide Synthesis," (Bodansky and Trost, ed.), Springer-Verlag, Inc. N.Y., (1993). Proteins or peptides of the invention may comprise one or more non-naturally occurring or modified amino acids. A "non-naturally occurring amino acid residue" refers to a residue, other than those naturally occurring amino acid residues listed above, which is able to covalently bind adjacent amino acid residues(s) in a polypeptide chain. Non-natural amino acids include, but are not limited to homo-lysine, homo-arginine, homo-serine, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, citrulline, pentylglycine, pipecolic acid and thioproline. Modified amino acids include natural and non-natural amino acids which are chemically blocked, reversibly or irreversibly, or modified on their N-terminal amino group or their side chain groups, as for example, N-methylated D and L amino acids, side chain functional groups that are chemically modified to another functional group. For example, modified amino acids include methionine sulfoxide; methionine sulfone; aspartic acid- (beta-methyl ester), a modified amino acid of aspartic acid; N-ethylglycine, a modified amino acid of glycine; or alanine carboxamide and a modified amino acid of alanine. Additional non-natural and modified amino acids, and methods of incorporating them into proteins and peptides, are known in the art (see, e.g., Sandberg et al., (1998) J. Med. Chem. 41: 2481-91; Xie and Schultz (2005) Curr. Opin. Chem. Biol. 9: 548-554; Hodgson and Sanderson (2004) Chem. Soc. Rev. 33: 422-430, Mandal, K. et al. Proc. Natl. Acad. Sci. USA; published online Aug. 27, 2012; doi:10.1073/pnas.1210483109).

Typically, the coding sequence for a VEGF/PSMA bifunctional protein or single chains thereof is placed under the control of a promoter that is functional in the desired host cell to produce relatively large quantities of the gene product. A wide variety of promoters is well-known, and can be used in the expression vectors of the invention, depending on the particular application. Ordinarily, the promoter selected depends upon the cell in which the promoter is to be active. Other expression control sequences such as ribosome binding sites, transcription termination sites and the like are also optionally included. Constructs that include one or more of these control sequences are termed "expression cassettes." Expression can be achieved in prokaryotic and eukaryotic cells utilizing promoters and other regulatory agents appropriate for the particular host cell. Exemplary host cells include, but are not limited to, *E. coli*, other bacterial hosts, yeast, and various higher eukaryotic cells such as the COS, CHO and HeLa cells lines and myeloma cell lines.

Polypeptides may be purified and identified using commonly known methods such as fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; hydrophobic affinity resins, ligand affinity using a suitable binding partner immobilized on a matrix, centrifugation, ELISA, BIACore, Western blot assay, amino acid and nucleic acid sequencing, and biological activity.

The polypeptide may be labeled, either directly or indirectly. Any of a variety of suitable labeling systems may be used, including but not limited to, radioisotopes such as $^{125}I$; enzyme labeling systems that generate a detectable colorimetric signal or light when exposed to substrate; and fluorescent labels. Indirect labeling involves the use of a protein, such as a labeled antibody, that specifically binds to the polypeptide of interest. Such antibodies include but are not limited to polyclonal, monoclonal, chimeric, single chain, Fab fragments and fragments produced by a Fab expression library.

Once expressed, the recombinant polypeptides can be purified according to standard procedures of the art, including ammonium sulfate precipitation, affinity columns, ion exchange and/or size exclusivity chromatography, gel electrophoresis and the like (see, generally, R. Scopes, Protein Purification, Springer-Verlag, N.Y. (1982), Deutscher, Methods in Enzymology Vol. 182: Guide to Protein Purification., Academic Press, Inc. N.Y. (1990)).

The polypeptides of the invention can be coupled or conjugated to one or more cytotoxic or imaging moieties. As used herein, "cytotoxic moiety" is a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof. "Imaging moiety" (I) is a moiety that can be utilized to increase contrast between a tumor and the surrounding healthy tissue in a visualization technique (e.g., radiography, positron-emission tomography, single-photon emission computed tomography, near-infrared fluorescence imaging, magnetic resonance imaging, ultrasound, direct or indirect visual inspection). Thus, suitable imaging moieties include radiography moieties (e.g. heavy metals and radiation emitting moieties), positron emitting moieties, magnetic resonance contrast moieties, gas-filled mirobubble spheres for contrast-enhanced ultrasound, and optically visible moieties (e.g., fluorescent or visible-spectrum dyes, visible particles, etc.). It will be appreciated by one of ordinary skill that some overlap exists between therapeutic and imaging moieties. For instance $^{212}$Pb and $^{212}$Bi are both useful radioisotopes for therapeutic compositions, but are also electron-dense, and thus provide contrast for X-ray radiographic imaging techniques, and can also be utilized in scintillation imaging techniques.

In general, therapeutic or imaging agents may be conjugated to the polypeptides of the invention by any suitable technique, with appropriate consideration of the need for pharmokinetic stability and reduced overall toxicity to the patient. A therapeutic agent may be coupled to a polypeptide either directly or indirectly (e.g. via a linker group). A direct reaction between an agent and a polypeptide is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer to distance a polypeptide from an agent in order to avoid interference with binding capabilities. A linker group can also serve to increase the chemical reactivity of a substituent on a moiety or a polypeptide, and thus increase the coupling efficiency. An increase in chemical reactivity may also facilitate the use of moieties, or functional groups on moieties, which otherwise would not be possible.

Suitable linkage chemistries include maleimidyl linkers and alkyl halide linkers (which react with a sulfhydryl on the polypeptide moiety) and succinimidyl linkers (which react with a primary amine on the polypeptide moiety). Several primary amine and sulfhydryl groups are present on a polypeptide, and additional groups may be designed into recombinant molecules. It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology, e.g., U.S. Pat. No. 4,671,958. As an alternative coupling method, cytotoxic or imaging moieties may be coupled to the polypeptides of the invention through an oxidized carbohydrate group at a glycosylation site, as described in U.S. Pat. Nos. 5,057,313 and 5,156,840. Yet another alternative method of coupling a polypeptide to the cytotoxic or imaging moiety is by the use of a non-covalent binding pair, such as streptavidin/biotin, or avidin/biotin. In these embodiments, one member of the pair is covalently coupled to a polypeptide and the other member of the binding pair is covalently coupled to the cytotoxic or imaging moiety.

Carriers and linkers specific for radionuclide agents (both for use as cytotoxic moieties or positron-emission imaging moieties) include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. Such chelation carriers are also useful for magnetic spin contrast ions for use in magnetic resonance imaging tumor visualization methods, and for the chelation of heavy metal ions for use in radiographic visualization methods.

Preferred radionuclides for use as cytotoxic moieties are radionuclides that are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters. $^{123}$I, $^{125}$I, $^{131}$I, or $^{211}$At may be conjugated to polypeptides of the invention for use in the compositions and methods utilizing any of several known conjugation reagents, including Iodogen, N-succinimidyl 3-[$^{211}$At]astatobenzoate, N-succinimidyl 3-[$^{131}$I]iodobenzoate (SIB), and N-succinimidyl 5-[$^{131}$I]iodob-3-pyridinecarboxylate (SIPC). Any iodine isotope may be utilized in the recited iodo-reagents. Radionuclides can be conjugated to polypeptides of the invention by suitable chelation agents known to those of skill in the nuclear medicine arts.

Preferred radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Examples of such compositions, which may be utilized for x-ray radiography are described in U.S. Pat. No. 5,709,846, incorporated fully herein by reference. Such moieties may be conjugated to the polypeptides of the invention through an acceptable chemical linker or chelation carrier. In addition, radionuclides which emit radiation capable of penetrating the skull may be useful for scintillation imaging techniques. Suitable radionuclides for conjugation include $^{99}$Tc, $^{111}$In, and $^{67}$Ga. Positron emitting moieties for use in the present invention include $^{18}$F, which can be easily conjugated by a fluorination reaction with the polypeptides of the invention according to the method described in U.S. Pat. No. 6,187,284, or $^{64}$Cu, which can be conjugated through chemical chelators as extensively described in the literature.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred. Examples of such chelates, suitable for magnetic resonance spin imaging, are described in U.S. Pat. No. 5,733,522, incorporated fully herein by reference. Nuclear spin contrast chelates may be conjugated to the polypeptides of the invention through a suitable chemical linker.

Optically visible moieties for use as imaging moieties include fluorescent dyes, or visible-spectrum dyes, visible particles, and other visible labeling moieties. Fluorescent dyes such as ALEXA dyes, fluorescein, coumarin, rhodamine, bodipy Texas red, and cyanine dyes, are useful when sufficient excitation energy can be provided to the site to be inspected visually. Endoscopic visualization procedures may be more compatible with the use of such labels. For many procedures where imaging agents are useful, such as during an operation to resect a brain tumor, visible spectrum dyes are preferred. Acceptable dyes include FDA-approved food dyes and colors, which are non-toxic, although pharmaceutically acceptable dyes which have been approved for internal administration are preferred. In preferred embodiments, such dyes are encapsulated in carrier moieties, which are in turn conjugated to the polypeptides of the invention. Alternatively, visible particles, such as colloidal gold particles or latex particles, may be coupled to the polypeptides of the invention via a suitable chemical linker.

Pharmaceutical Formulations

Formulations of polypeptides of the invention find use in diagnosis and therapy. The formulation may comprise one, two or more polypeptides of the invention. The therapeutic formulation may be administered in combination with other methods of treatment, e.g. chemotherapy, radiation therapy, surgery, and the like.

Formulations may be optimized for retention and stabilization at a targeted site. Stabilization techniques include enhancing the size of the polypeptide, by cross-linking, multimerizing, or linking to groups such as polyethylene glycol, polyacrylamide, neutral protein carriers, etc. in order to achieve an increase in molecular weight. Other strategies for increasing retention include the entrapment of the polypeptide in a biodegradable or bioerodible implant. The rate of release of the therapeutically active agent is controlled by the rate of transport through the polymeric matrix, and the biodegradation of the implant. The transport of polypeptide through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. The polypeptide may be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred.

The data obtained from cell culture and/or animal studies can be used in formulating a range of dosages for humans. The dosage of the active ingredient typically lines within a range of circulating concentrations that include the $ED_{50}$ with low toxicity. The dosage can vary within this range depending upon the dosage form employed and the route of administration utilized.

The pharmaceutical compositions described herein can be administered in a variety of different ways. Examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods.

Formulations suitable for parenteral administration, such as, for example, by intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Nucleic Acids

Nucleic acid sequences encoding polypeptides of the invention find use in the recombinant production of the encoded polypeptide, and the like. One of skill in the art can readily utilize well-known codon usage tables and synthetic methods to provide a suitable coding sequence for any of the polypeptides of the invention. Direct chemical synthesis methods include, for example, the phosphotriester method of Narang et al. (1979) Meth. Enzymol. 68: 90-99; the phosphodiester method of Brown et al. (1979) Meth. Enzymol. 68: 109-151; the diethylphosphoramidite method of Beaucage et al. (1981) Tetra. Lett., 22: 1859-1862; and the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. While chemical synthesis of DNA is often limited to sequences of about 100 bases, longer sequences can be obtained by the ligation of shorter sequences. Alternatively, subsequences may be cloned and the appropriate subsequences cleaved using appropriate restriction enzymes.

The nucleic acids of the subject invention are isolated and obtained in substantial purity, generally as other than an intact chromosome. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art, such as transferrin polycation-mediated DNA transfer, transfection with naked or encapsulated nucleic acids, liposome-mediated DNA transfer, intracellular transportation of DNA-coated latex beads, protoplast fusion, viral infection, electroporation, gene gun, calcium phosphate-mediated transfection, and the like.

Methods of Use

Molecular imaging unites molecular biology and in vivo imaging. It enables the visualisation of the cellular function and the follow-up of the molecular process in living organisms without perturbing them.

in some embodiments, the methods are adapted for imaging use in vivo, e.g., to locate or identify sites where angiogenic cells are present. In these embodiments, a detectably-labeled polypeptide of the invention is administered to an individual (e.g., by injection), and labeled cells are located using standard imaging techniques, including, but not limited to, near-infrared fluorescence imaging, positron emission tomography, magnetic resonance imaging, computed tomography scanning, and the like.

For diagnostic in vivo imaging, the type of detection instrument available is a major factor in selecting a given radionuclide. The radionuclide chosen must have a type of decay that is detectable by a given type of instrument. In general, any conventional method for visualizing diagnostic imaging can be utilized in accordance with this invention. Another important factor in selecting a radionuclide for in vivo diagnosis is that its half-life be long enough that it is still detectable at the time of maximum uptake by the target tissue, but short enough that deleterious radiation of the host is minimized. A currently used method for labeling with $^{99m}$Tc is the reduction of pertechnetate ion in the presence of a chelating precursor to form the labile $^{99m}$Tc-precursor complex, which, in turn, reacts with the metal binding group of a bifunctionally modified chemotactic peptide to form a $^{99m}$Tc-chemotactic peptide conjugate. In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy (γ-ray) emissions of the specific isotopes employed and the sensitivity and sophistication of the instruments used to detect them, the two-dimensional distribution of radioactivity may be inferred from outside of the body. Among the most commonly used positron-emitting nuclides in PET are included $^{11}$C, $^{13}$N, $^{15}$O, and $^{18}$F, and $^{64}$Cu. Isotopes that decay by electron capture and/or γ emission are used in SPECT, and include $^{123}$I and $^{99m}$Tc, and $^{111}$In.

Therapeutic Methods

The dose of a polypeptide of the invention administered to a subject, particularly a human, in the context of the present invention should be sufficient to effect a therapeutic reduction in angiogenesis in the subject over a reasonable time frame. The dose will be determined by, among other considerations, the potency of the particular polypeptide of the invention employed and the condition of the subject, as well as the body weight of the subject to be treated. The size of the dose also will be determined by the existence, nature, and extent of any adverse side-effects that might accompany the administration of a particular compound.

In determining the effective amount of polypeptide in the reduction of angiogenesis, the route of administration, the kinetics of the release system (e.g., pill, gel or other matrix), and the potency of the antagonist are considered so as to achieve the desired anti-angiogenic effect with minimal adverse side effects. The polypeptide of the invention will typically be administered to the subject being treated for a time period ranging from a day to a few weeks, consistent with the clinical condition of the treated subject.

Regardless of the route of administration, the dose of polypeptide of the invention can be administered over any appropriate time period, e.g., over the course of 1 to 24 hours, over one to several days, etc. Furthermore, multiple doses can be administered over a selected time period. A suitable dose can be administered in suitable subdoses per day, particularly in a prophylactic regimen. The precise treatment level will be dependent upon the response of the subject being treated.

In some embodiments, a polypeptide of the invention is administered in a combination therapy with one or more other therapeutic agents, including an inhibitor of angiogenesis; and a cancer chemotherapeutic agent.

Suitable chemotherapeutic agents include, but are not limited to, alkylating agents, e.g. Cisplatin, Cyclophosphamide, Altretamine; DNA strand-breakage agents, such as Bleomycin; DNA topoisomerase II inhibitors, including intercalators, such as Amsacrine, Dactinomycin, Daunorubicin, Doxorubicin, Idarubicin, and Mitoxantrone; nonintercalating topoisomerase II inhibitors such as, Etoposide and Teniposide; DNA minor groove binder Plicamycin; alkylating agents, including nitrogen mustards such as Chlorambucil, Cyclophosphamide, Isofamide, Mechlorethamine, Melphalan, Uracil mustard; aziridines such as Thiotepa; methanesulfonate esters such as Busulfan; nitroso ureas, such as Carmustine, Lomustine, Streptozocin; platinum complexes, such as Cisplatin, Carboplatin; bioreductive alkylator, such as Mitomycin, and Procarbazine, Dacarbazine and Altretamine; antimetabolites, including folate antagonists such as Methotrexate and trimetrexate; pyrimidine antagonists, such as Fluorouracil, Fluorodeoxyuridine, CB3717, Azacytidine, Cytarabine; Floxuridine purine antagonists including Mercaptopurine, 6-Thioguanine, Fludarabine, Pentostatin; sugar modified analogs include Cyctrabine, Fludarabine; ribonucleotide reductase inhibitors including hydroxyurea; tubulin interactive agents including Vincristine Vinblastine, and Paclitaxel; adrenal corticosteroids such as Prednisone, Dexamethasone, Methylprednisolone, and Prodnisolone; hormonal blocking agents including estrogens, conjugated estrogens and Ethinyl Estradiol and Diethylstilbesterol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone estrogens, conjugated estrogens and Ethinyl Estradiol and Diethylstilbesterol, Chlorotrianisene and Idenestrol; progestins such as Hydroxyprogesterone caproate, Medroxyprogesterone, and Megestrol; androgens such as testosterone, testosterone propionate; fluoxymesterone, methyltestosterone; and the like.

The polypeptide of the invention may be administered with other anti-angiogenic agents. Anti-angiogenic agents include, but are not limited to, angiostatic steroids such as heparin derivatives and glucocorticosteroids; thrombospondin; cytokines such as IL-12; fumagillin and synthetic derivatives thereof, such as AGM 12470; interferon-$\alpha$; endostatin; soluble growth factor receptors; neutralizing monoclonal antibodies directed against growth factors such as vascular endothelial growth factor; and the like.

In some embodiments, a VEGF/PSMA bifunctional protein and the additional therapeutic agent are administered in a unified dosage form or in separate dosage forms. In some embodiments, the methods comprise administration of a VEGF/PSMA bifunctional protein disclosed herein in combination with a therapeutic procedure. The benefit experienced by an individual may be increased by administering one of the therapeutic agents described herein with another therapeutic agent (which also includes a therapeutic regimen) that also has therapeutic benefit. In any case, regardless of the disease or disorder being treated, the overall benefit experienced by the patient is simply additive of the two therapeutic agents or in other embodiments, the patient experiences a synergistic benefit.

The particular choice of agents used will depend upon the diagnosis of the attending physicians and their judgment of the condition of the patient and the appropriate treatment protocol. The agents are optionally administered concurrently (e.g., simultaneously, essentially simultaneously or within the same treatment protocol) or sequentially, depending upon the nature of the disorder, the condition of the patient, and the actual choice of agents used. The determination of the order of administration, and the number of repetitions of administration of each therapeutic agent during a treatment protocol, is based on an evaluation of the disease being treated and the condition of the patient.

In some embodiments, therapeutically-effective dosages vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

The instant invention provides a method of reducing angiogenesis in a mammal. The method generally involves administering to a mammal a polypeptide of the invention in an amount effective to reduce angiogenesis. An effective amount of an polypeptide of the invention reduces angiogenesis by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, or more, when compared to an untreated (e.g., a placebo-treated) control.

Whether angiogenesis is reduced can be determined using any known method. Methods of determining an effect of an agent on angiogenesis are known in the art and include, but are not limited to, inhibition of neovascularization into implants impregnated with an angiogenic factor; inhibition of blood vessel growth in the cornea or anterior eye chamber; inhibition of endothelial cell proliferation, migration or tube formation in vitro; the chick chorioallantoic membrane assay; the hamster cheek pouch assay; the polyvinyl alcohol sponge disk assay. Such assays are well known in the art and have been described in numerous publications, including, e.g., Auerbach et al. ((1991) *Pharmac. Ther.* 51:1-11), and references cited therein.

The invention further provides methods for treating a condition or disorder associated with or resulting from pathological angiogenesis. In the context of cancer therapy, a reduction in angiogenesis according to the methods of the invention effects a reduction in tumor size; and a reduction in tumor metastasis. Whether a reduction in tumor size is achieved can be determined, e.g., by measuring the size of the tumor, using standard imaging techniques. Whether metastasis is reduced can be determined using any known method. Methods to assess the effect of an agent on tumor size are well known, and include imaging techniques such as computerized tomography and magnetic resonance imaging.

The instant methods are useful in the treatment of both primary and metastatic solid tumors, including carcinomas, sarcomas, leukemias, and lymphomas. Of particular interest is the treatment of prostate tumors occurring at a site of angiogenesis. In addition, the instant methods are useful for reducing metastases from the tumors described above either when used alone or in combination with radiotherapy and/or other chemotherapeutic agents.

In some embodiments, the dose of a pharmaceutical composition comprising a VEGF/PSMA bifunctional protein is administered to a subject, particularly a human, is sufficient to effect a therapeutic reduction in angiogenesis in the subject over a reasonable time frame. In some embodiments, the dose is determined by the potency of the particular peptide employed and the condition of the subject, as well as the body weight of the subject to be treated. The size of the dose also will be determined by the existence, nature, and extent of any adverse side-effects that might accompany the administration of a particular compound.

It will be appreciated that the amount of a pharmaceutical composition comprising a VEGF/PSMA bifunctional protein disclosed herein required for use in treatment will vary with the route of administration, the nature of the condition for which treatment is required, and the age, body weight and condition of the patient, and will be ultimately at the discretion of the attendant physician or veterinarian. Compositions will typically contain an effective amount of the active agent(s), alone or in combination. In some embodiments, preliminary doses are determined according to animal tests, and the scaling of dosages for human administration are performed according to art-accepted practices.

In determining the effective amount of a VEGF/PSMA bifunctional protein, the route of administration, the kinetics of the release system (e.g., pill, gel or other matrix), and the potency of the antagonist are considered so as to achieve the desired effect with minimal adverse side effects.

The dosage of a VEGF/PSMA bifunctional protein is adjusted according to the potency and/or efficacy relative to a VEGF antagonist. In some embodiments, a dose is in the range of about 0.001 μg to 100 mg, given 1 to 20 times daily, and be up to a total daily dose of about 0.01 μg to 100 mg. In some embodiments, if applied topically, for the purpose of a systemic effect, the patch or cream is designed to provide for systemic delivery of a dose in the range of about 0.01 μg to 100 mg. In some embodiments, if injected for the purpose of a systemic effect, the matrix in which the VEGF/PSMA bifunctional protein is administered is designed to provide for a systemic delivery of a dose in the range of about 0.001 μg to 1 mg. If injected for the purpose of a local effect, the matrix is designed to release locally an amount of VEGF/PSMA bifunctional protein in the range of about 0.001 μg to 100 mg.

In some embodiments, dosage ranges for a pharmaceutical composition comprising a VEGF/PSMA bifunctional protein described herein are determined by the ordinarily skilled artisan, and are, e.g., first be determined in animal models for determining dosage, safety and efficacy according to standard methods known in the art.

In some embodiments, a therapeutically effective amount of a pharmaceutical composition comprising a VEGF variant polypeptide is expressed as mg of the VEGF/PSMA bifunctional protein per kg of subject body mass. In some embodiments, a therapeutically effective amount is 1-1,000 mg/kg, 1-500 mg/kg, 1-250 mg/kg, 1-100 mg/kg, 1-50 mg/kg, 1-25 mg/kg, or 1-10 mg/kg. In some embodiments, an effective amount is 5 mg/kg, 10 mg/kg, 25 mg/kg, 50 mg/kg, 75 mg/kg, 100 mg/kg, 150 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1,000 mg/kg, about 5 mg/kg, about 10 mg/kg, about 25 mg/kg, about 50 mg/kg, about 75 mg/kg, about 100 mg/kg, about 150 mg/kg, about 200 mg/kg, about 250 mg/kg, about 300 mg/kg, about 400 mg/kg, about 500 mg/kg, about 600 mg/kg, about 700 mg/kg, about 800 mg/kg, about 900 mg/kg, or about 1,000 mg/kg.

In some embodiments, a therapeutically effective amount is expressed as mg of the compound per square meter of subject body area. In some embodiments, a pharmaceutical composition comprising a VEGF/PSMA bifunctional protein is administered subcutaneously in a range of doses, for example 1 to 1500 mg (0.6 to 938 mg/m$^2$), or 2 to 800 mg (1.25 to 500 mg/m$^2$), or 5 to 500 mg (3.1 to 312 mg/m$^2$), or 2 to 200 mg (1.25 to 125 mg/m$^2$) or 10 to 1000 mg (6.25 to 625 mg/m$^2$), particular examples of doses including 10 mg (6.25 mg/m$^2$), 20 mg (12.5 mg/m$^2$), 50 mg (31.3 mg/m$^2$), 80 mg (50 mg/m$^2$), 100 mg (62.5 mg/m$^2$), 200 mg (125 mg/m$^2$), 300 mg (187.5 mg/m$^2$), 400 mg (250 mg/m$^2$), 500 mg (312.5 mg/m$^2$), 600 mg (375 mg/m$^2$), 700 mg (437.5 mg/m$^2$), 800 mg (500 mg/m$^2$), 900 mg (562.5 mg/m$^2$) and 1000 mg (625 mg/m$^2$).

In some embodiments, a pharmaceutical composition comprising a VEGF/PSMA bifunctional protein described herein is administered for prophylactic and/or therapeutic treatments. In therapeutic applications, a pharmaceutical composition comprising a VEGF/PSMA bifunctional protein is administered to an individual already suffering from a disorder, in an amount sufficient to cure or at least partially arrest the symptoms of the disorder. Amounts effective for this use will depend on the severity and course of the disorder, previous therapy, the patient's health status, weight, and response to the drugs, and the judgment of the treating physician.

In some embodiments, a pharmaceutical composition comprising a VEGF/PSMA bifunctional protein is administered to the patient on a regular basis, e.g., three times a day, two times a day, once a day, every other day or every 3 days. In other embodiments, a pharmaceutical composition comprising a VEGF/PSMA bifunctional protein is administered to the patient on an intermittent basis, e.g., twice a day followed by once a day followed by three times a day; or the first two days of every week; or the first, second and third day of a week. In some embodiments, intermittent dosing is as effective as regular dosing. In the case wherein the patient's condition does not improve, upon the doctor's discretion the administration of a pharmaceutical composition comprising a VEGF/PSMA bifunctional protein is administered chronically, that is, for an extended period of time, including throughout the duration of the patient's life in order to ameliorate or otherwise control or limit the symptoms of the patient's disorder.

In the case wherein the patient's status does improve, upon the doctor's discretion the administration of a pharmaceutical composition comprising a VEGF/PSMA bifunctional protein is given continuously; alternatively, the dose of drug being administered is temporarily reduced or temporarily suspended for a certain length of time (i.e., a "drug holiday"). In some embodiments, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder is retained. In some embodiments, patients require intermittent treatment on a long-term basis upon any recurrence of symptoms.

The amount of a given agent that will correspond to such an amount will vary depending upon factors such as, disorder and its severity, the identity (e.g., weight) of the subject or host in need of treatment, and is determined according to the particular circumstances surrounding the case, including, for example, the specific pharmaceutical composition comprising a VEGF/PSMA bifunctional protein being administered, the route of administration, the condition being treated, and the subject or host being treated. The desired dose is conveniently presented in a single dose or as divided doses administered simultaneously (or over a short period of time) or at appropriate intervals, for example as two, three, four or more sub-doses per day.

Kits

Disclosed herein, in certain embodiments, are kits comprising a VEGF/PSMA bifunctional protein derivative thereof.

The kits, regardless of type, will generally include one or more containers into which the biological agents are placed and, preferably, suitably aliquoted. In some embodiments, the components of the kits are packaged either in aqueous media or in lyophilized form.

In a further embodiment, the present invention provides kits containing a VEGF/PSMA bifunctional protein or derivative thereof, which are used, for instance, for therapeutic or non-therapeutic applications. The kit comprises a container with a label. Suitable containers include, for example, bottles, vials, and test tubes. In some embodiments, the containers are formed from a variety of materials such as glass or plastic. The container holds a composition which includes a VEGF/PSMA bifunctional protein that is effective for therapeutic or non-therapeutic applications, such as described above. The label on the container indicates that the composition is used for a specific therapy or non-therapeutic application, and also indicates directions for either in vivo or in vitro use, such as those described above.

The kit will typically comprise the container described above and one or more other containers comprising materials desirable from a commercial and user standpoint, including buffers, diluents, filters, needles, syringes, and package inserts with instructions for use. In some embodiments, the kit also includes a control consisting of wild-type VEGF.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. In the following, examples will be described to illustrate parts of the invention.

EXAMPLES

Example 1

Using the strategy of engineering a bispecific protein using a naturally bivalent, non-antibody scaffold, a bispecific reagent that specifically binds to PSMA and VEGFR2 is provided. The non-antibody scaffold is comparable in size to smaller antibody constructs such as scFvs and nanobodies and optimal for applications in which this size range is a desired characteristic. By starting with a bivalent molecule, two binding sites are identified that can be readily mutated without disrupting the overall scaffold structure. In addition, a bivalent scaffold allows shifting from a monospecific to a bispecific molecule without doubling the size of the final protein construct.

$VEGF_{121}$ was selected as the bivalent scaffold. $VEGF_{121}$ is a ~14 kDa protein that occurs as a covalently linked homodimer (FIG. 1). Each monomer is arranged in a head-to-tail orientation relative to the other, with a cystine-knot at both ends of the dimer. Near each cystine-knot is an inter-chain disulfide bond that links the two monomers. In a biological context, the homodimer activates its receptors VEGFR1 and VEGFR2 by binding two receptor molecules simultaneously, leading to receptor transphosphorylation and pathway activation. Instead of each monomer forming a complete binding site for VEGFR1/2, the receptor binding sites are located at opposite ends of the homodimer with essential residues contributed by both monomers. Many of these residues are located in three unstructured loops on either side of the homodimer, with two loops contributed by one monomer and a third loop contributed by the other. Accordingly, $VEGF_{121}$ monomer is unable to bind and activate its receptors. The cystine-knot motif is responsible for the high thermal ($T_m$>100° C.) and chemical (Gdn HCl $c_{1/2}$=4.3M) stability of the protein. $VEGF_{121}$'s high stability, expressibility in recombinant systems, and symmetrical bivalent structure make it a good system for engineering bispecificity.

$VEGF_{121}$, when expressed as a monomer, easily forms a covalent homodimer in solution. In anticipation of converting the molecule into a heterodimer, a single-chain homodimer was created by adding a $(Gly_4Ser)_4$ linker between the C-terminus of one monomer and the N-terminus of the other. This allows proper partnering between monomers whose binding residues are simultaneously evolved. Next, alanine mutations to one end of the homodimer eliminates binding to VEGFR2 on that end. Since VEGFR2 is activated through dimerization and trans-phosphorylation, this new VEGF heterodimer is an antagonist that binds a single copy of VEGFR2 and prevents receptor dimerization. The single-chain antagonist mutant VEGF is termed scVEGFmut. Relative to the native VEGF121 protein, VEGFmut has four mutations corresponding to key binding residues at one pole of the molecules: chain 1 F17A, E64A; chain 2 I46A, I83A (FIG. 1A) (note that residue numbers correspond to the residue numbers from VEGF121, reference sequence is provided as SEQ ID NO:1, not positions in scVEGF).

scVEGFmut is able to tolerate extreme mutagenesis on all three of its binding loops on one end without completely eliminating expression or folding, as analyzed by VEGFR2 binding to the non-mutated end. The extent of protein expressibility and folding depends on which register of each loop was mutated and the length of the substituted amino acid sequence.

Protein engineering. The NDAGL register of Loop 1 was lengthened by one amino acid, while DEIEY in Loop 2 and IFKGH in Loop 3 were lengthened by four amino acids. Loop 1 is in the first monomer, while Loops 2 and 3 are in the second monomer. Each randomized sequence was encoded in primers by NNS codons, where N=any base and S=C or G. This allows for all amino acids while reducing the probability of stop codons. The library was created using a protocol adapted from Lipovšek et al. in which the entire gene is constructed using overlapping primers. The loop library was cloned into the yeast surface display plasmid pCTCON2 and transformed into the *Saccharomyces cerevisiae* strain EBY100 for a final diversity of about $1\times10^8$. This plasmid enables expression of the scVEGFmut library on the yeast cell surface through genetic linkage to the yeast agglutinin protein Aga2. scVEGFmut is surrounded by an N-terminal hemagglutinin (HA) tag and a C-terminal c-Myc tag, which allows for detection of full-length protein. Proper folding of the scVEGFmut variants were analyzed by binding to VEGFR2-Fc.

Two rounds of affinity selection were initially performed, and it was found that changes in the sequence of loop 2 and loop 3 were required for binding to PSMA. The loop 1 of the best variants from each library was reverted back to the wild-type sequence, to lessen any folding or stability challenges for the scVEGFmut scaffold.

An additional round of mutagenesis was performed for the VEGFR2/PSMA binder with error-prone PCR on the entire gene. The library diversity was $2.5\times10^7$. After several rounds of sorting, we sequenced the variants. The amino acid changes that were found are shown below in Table 1.

There were several mutations that occurred more than once, but only one consensus mutation appeared, Q89R or Q89K (numbering made with reference to VEGF121, SEQ ID NO:1). This residue occurs right after the randomized Loop 3 in the second monomer. Its location suggests that it either helps stabilize the loop in the context of the scVEGFmut scaffold or participates in PSMA binding, leading to a higher affinity than was found in the second round of sorting. There were also several mutations that appeared in multiple variants but were not consensus. Mutations that appeared in multiple variants are believed to be important for binding as they appeared multiple times in selection.

TABLE 1

Changes in Chain 1 and linker (numbering made relative to reference sequence of VEGF121 (SEQ ID NO:1))

| repeats | AA changes | Disordered pos. 13 | Helix pos. 22 | Helix aft. strand 1 pos. 36 | Loop (WT) Pos. 45 | Strand 3 Pos. 71 | Strand 3 Pos. 80 | Loop (WT) Pos. 84 | Strand 4 Pos. 91 | Strand 4 Pos. 100 | n/a | n/a | n/a |
|---|---|---|---|---|---|---|---|---|---|---|---|---|---|
| 0 | 0 | E | Q | F | Y | T | I | K | I | N | G | G | G |
| 16 | 1 | — | — | — | — | — | — | — | — | — | — | — | — |
| 2 | 4 | — | — | L | — | — | — | — | — | — | S | — | — |
| 1 | 2 | A | — | — | — | — | — | — | — | — | — | — | — |
| 1 | 2 | — | — | — | — | — | — | — | — | — | — | — | V |
| 1 | 2 | — | — | L | — | — | — | — | — | — | — | — | — |
| 1 | 2 | — | — | — | — | — | — | — | — | — | — | — | — |
| 1 | 2 | G | — | — | — | — | — | — | — | — | — | — | — |
| 1 | 2 | — | — | — | — | — | — | — | — | — | — | S | — |
| 1 | 2 | — | — | — | — | A | — | — | — | — | — | — | — |
| 1 | 2 | — | — | — | — | — | — | R | — | — | — | — | — |
| 1 | 2 | — | — | — | — | — | — | — | — | — | S | — | — |
| 1 | 2 | — | — | — | — | — | — | — | V | — | — | — | — |
| 1 | 2 | — | — | — | — | — | V | — | — | — | — | — | — |
| 1 | 2 | — | — | — | — | — | — | — | — | — | — | — | — |
| 2 | 3 | — | R | — | — | — | V | — | — | — | — | — | — |
| 1 | 2 | — | — | — | H | — | — | — | — | — | — | — | — |
| 1 | 4 | — | — | — | — | A | — | — | — | S | — | — | — |

Changes in chain 2 (numbering made relative to reference sequence of VEGF121)

Changes in Chain 2 (numbering made relative to reference sequence of VEGF121)

| Helix Pos. 22 | strand 1 Pos. 29 | Loop 2 n/a | strand 4 Pos. 89 | strand 4 Pos. 92 | Disordered Pos. 109 |
|---|---|---|---|---|---|
| Q | I | N | Q | G | D |
| — | — | — | R | — | — |
| — | — | S | K | — | — |
| — | — | — | R | — | — |
| — | — | — | R | — | — |
| — | — | — | R | — | — |
| — | T | — | R | — | — |
| — | — | — | R | — | — |
| — | — | — | R | — | — |
| — | — | — | K | — | — |
| — | — | — | R | — | — |
| — | — | — | R | — | — |
| — | — | — | R | — | — |
| — | — | — | R | — | — |
| R | — | — | R | — | — |
| — | — | — | — | R | — |
| — | — | — | R | — | — |
| — | — | — | R | — | G |

Yeast surface affinity. On yeast, the binding affinity of scVEGFmut and each variant to VEGFR2-Fc and their target proteins were determined. The affinity for the mutated variants for VEGFR2-Fc did not differ more than an order of magnitude from that of scVEGFmut, suggesting that engineering one end of the homodimer did not greatly alter the functionality of the other. The affinity of the VEGFR2/PSMA proteins to their target proteins were in the mid to low-nanomolar range.

Purification. scVEGFmut and all variants were cloned into the ppic9k vector and transformed into the *Pichia pastoris* strain GS115. Cells were induced with methanol for three days and proteins were purified using a nickel-NTA affinity column and size exclusion.

Soluble affinity. The Octet® platform was used to measure the soluble affinity of the variants to VEGFR2-Fc and their respective target proteins. As with the results on the yeast surface, the variants' affinities to VEGFR2-Fc were similar to each other and to scVEGFmut. Since the variants were not evolved for high affinity toward VEGFR2, this would again indicate that mutating the opposite end did not interfere with functionality of the VEGFR2-binding end.

CD analysis. The CD spectra of scVEGFmut is similar to that of wild-type VEGF in suggesting an overall β-sheet structure. The spectra of VEGFR2/PSMA variant appeared similar, indicating that the secondary structure for both proteins are similar. We then performed thermal denaturation melts and guanidine hydrochloride (Gdn HCl) denaturation. The melts for scVEGFmut were consistent with the values found in previous literature. The $T_m$ value for wild-type VEGF was over 100° C.; unsurprisingly, there was no decrease in normalized ellipticity at 222 nm even when the temperature was raised to 95° C. However, there was an upward trend in ellipticity. VEGFR2/PSMA demonstrated almost identical chemical denaturation curves compared to scVEGFmut and underwent the same change in ellipticity at high temperatures. We also confirmed that the Gdn HCl melt is reversible for all proteins. Our results suggest that the secondary structure, thermal/chemical stability, and protein folding are unchanged between scVEGFmut and the mutated variants.

Although the foregoing invention and its embodiments have been described in some detail by way of illustration and example for purposes of clarity of understanding, it is readily apparent to those of ordinary skill in the art in light of the teachings of this invention that certain changes and modifications may be made thereto without departing from the spirit or scope of the appended claims. Accordingly, the preceding merely illustrates the principles of the invention. It will be appreciated that those skilled in the art will be able to devise various arrangements which, although not explicitly described or shown herein, embody the principles of the invention and are included within its spirit and scope.

What is claimed is:

1. A prostate specific membrane antigen (PSMA) binding polypeptide, comprising:

a polypeptide identical or essentially similar to human VEGF-A, in which each of loops 2 and loop 3 of the VEGF-A sequence are replaced with a peptide motif that provides for specific binding to PSMA, wherein the loop 2 sequence is replaced with the binding motif SIASWNPWM (SEQ ID NO: 7) or a conservative variant thereof and the loop 3 sequence is replaced with a binding motif selected from NRLFRYLPV (SEQ ID NO: 8) or SYLKFWIRW(SEQ ID NO: 9) or a conservative variant thereof.

2. The polypeptide of claim 1, in which the loop 2 sequence of the VEGF-A polypeptide corresponds to residues 41-45 of SEQ ID NO: 1.

3. The polypeptide of claim 2, in which the loop 3 sequence of the VEGF-A polypeptide corresponds to residues 83-88 of SEQ ID NO: 1.

4. The polypeptide of claim 3, further comprising amino acid substitution Q89R or Q89K, where amino acid numbering is made relative to reference sequence SEQ ID NO:1.

5. The polypeptide of claim 4, further comprising amino acid substitution 146A where amino acid numbering is relative to reference sequence SEQ ID NO:1.

6. A bifunctional FEGFR binding protein, comprising the PSMA binding polypeptide of claim 1, joined to a first human VEGF polypeptide chain selected from human VEGF-A, human VEGF-B, human VEGF-C, human VEGF-D and human PIGF.

7. The bifunctional VEGFR binding protein of claim 6, wherein said first human VEGF polypeptide is human VEGF-A comprising amino acid substitutions F17A and E64A amino acid substitutions where amino acid numbering is relative to reference sequence SEQ ID NO:1.

8. The bifunctional VEGFR binding protein of claim 6, wherein said first human VEGF polypeptide is human VEGF-A comprising one or more amino acid substitutions F36L, T71A, 180V.

9. The PSMA binding peptide of claim 1, comprising an amino acid sequence set forth in SEQ ID NO:3 or SEQ ID NO:4.

10. A bifunctional protein comprising a VEGF polypeptide comprising an amino acid sequence set forth in SEQ ID NO:5 linked to a prostate specific membrane antigen (PSMA) binding polypeptide haying an amino acid sequence of SEQ ID NO:3.

11. A bifunctional VEGFR binding protein according to claim 6, wherein the protein is conjugated to one or more cytotoxic or imaging moieties.

12. A pharmaceutical composition comprising a bifunctional VEGFR binding protein according to claim 6, and a pharmaceutically acceptable excipient.

13. A method of inhibiting angiogenesis, the method comprising:

contacting endothelial cells associated with said angiogenesis with a dose of a polypeptide of claim 6 effective to inhibit angiogenesis.

14. The method of claim 13 wherein said contacting is performed in vivo.

15. The method of claim 14, wherein said angiogenesis is associated with a vascularized tumor.

16. The method of claim 15, wherein said tumor is a prostate cancer.

17. The bifunctional VEGFR binding protein of claim 6, wherein the first VEGF polypeptide is joined to the PSMA binding polypeptide through a peptide linker of 1-20 amino acids in length.

18. The bifunctional VEGFR binding protein of claim 17, wherein the peptide linker is selected from a peptide linker having a formula selected from: $(GS)_n$, wherein n is an integer from 6 to 15; $(G_2S)_n$, wherein n is an integer from 4 to 10; $(G_3S)_n$, wherein n is an integer from 3 to 8; $(G_4S)_n$, wherein n is an integer from 2 to 6; $(G)_n$ wherein n is an integer from 12 to 30; and $(S)_n$, wherein n is an integer from 12 to 30.

19. The bifunctional VEGFR binding protein of claim 6, wherein the first human VEGF polypeptide chain is a VEGF-A monomer selected from VEGF165, VEGF165b, VEGF145, VEGF189, and VEGF206.

20. The bifunctional VEGFR binding protein of claim 6, wherein the first human VEGF polypeptide chain is selected from the polypeptide of SEQ ID NO:1 and SEQ ID NO:2, and optionally comprises amino acid substitutions F36L, T71A and 180V.

21. The bifunctional VEGFR binding protein of claim 6, wherein the first human VEGF polypeptide chain is selected from the polypeptide of SEQ ID NO:5 or SEQ ID NO:6.

* * * * *